United States Patent [19]

Farris

[11] Patent Number: 5,220,699
[45] Date of Patent: Jun. 22, 1993

[54] SURGICAL FACE MASK SUPPORT APPARATUS AND METHOD

[76] Inventor: R. David Farris, 3795 SW. Chehalem Ave., Portland, Oreg. 97201

[21] Appl. No.: 918,618

[22] Filed: Jul. 27, 1992

[51] Int. Cl.⁵ ..................... A47C 20/00; A61M 16/00
[52] U.S. Cl. ............................... 5/636; 5/606; 5/638; 5/643; 2/9; 128/206.26; 128/200.24; 128/202.13; 128/845
[58] Field of Search ................... 5/636, 637, 638, 643, 5/644, 622, 606; 128/206.21, 206.22, 206.23, 206.26, 206.27, 200.24, 201.22, 201.23, 201.24, 201.25, 202.13, 845, 857, 858; 2/9, 410, 411, 413, 414, 424; 602/74

[56] References Cited

U.S. PATENT DOCUMENTS

| | | | |
|---|---|---|---|
| 802,505 | 10/1905 | Goldsmith | 2/9 |
| 1,035,217 | 8/1912 | McQuary, Jr. | |
| 1,105,127 | 7/1914 | Drager | |
| 1,960,544 | 5/1934 | Malcom | |
| 2,239,003 | 4/1941 | Jones | 5/638 |
| 2,561,931 | 7/1951 | Kleiser | 5/644 |
| 2,688,142 | 9/1954 | Jensen | 5/644 |
| 2,839,757 | 6/1958 | Gianola | |
| 2,945,731 | 7/1960 | Tutrone | 5/606 |
| 3,103,667 | 9/1963 | Rogowski | 2/9 |
| 3,787,895 | 1/1974 | Belvedere | 2/9 |
| 4,082,257 | 4/1978 | Strickland | 5/606 |
| 4,504,050 | 3/1985 | Osborne | 5/637 |
| 4,752,064 | 6/1988 | Voss | |
| 4,764,990 | 8/1988 | Markert | 2/429 |
| 4,937,880 | 7/1990 | Beard | 128/206.21 |
| 4,971,051 | 11/1990 | Toffolon | 128/206.26 |
| 5,050,594 | 9/1991 | Babb | 128/206.24 |

FOREIGN PATENT DOCUMENTS

| | | | |
|---|---|---|---|
| 449456 | 6/1948 | Canada | 2/9 |
| 261511 | 11/1926 | United Kingdom | 5/644 |

Primary Examiner—Peter M. Cuomo
Assistant Examiner—Flemming Saether
Attorney, Agent, or Firm—John A. Beehner

[57] ABSTRACT

A facial support mask supports the face of a patient in the prone position during surgical procedures in spaced relation above a support surface and in a variety of selectively fixed positions relative to the torso and the support surface. The mask has a plurality of transversely spaced longitudinal crescent arms; at least one cross-strut interconnected with the longitudinal crescent arms; an inflatable chamber attached to the crescent arms and adapted to contact the patient's forehead and sides of his face; means and securement strap for securing the mask to the patient's face. The mask may also include an integral secretion collection dish for draining away secretions during the surgical procedure. The method includes providing a facial support mask for supporting a patient's face during surgical procedures in the prone position; anesthetizing the patient; placing said mask on patient's face such that no part of said mask contacts the patient's eyes, nose, or lips; securing said mask to patient's face; rolling the patient into the prone position; adjusting the inflation of the chamber to obtain correct inflation pressure; adjusting the patient's head orientation; and draining of any patient secretions.

10 Claims, 2 Drawing Sheets

SURGICAL FACE MASK SUPPORT APPARATUS AND METHOD

BACKGROUND OF THE INVENTION

1. Technical Field

The apparatus and method of the invention relate generally to the performance of surgical procedures. More specifically, they relate to an apparatus and method for protecting a patient's face during surgical procedures performed in the prone (face down) position while resting on a support surface.

It is well known in the art that a patient is especially vulnerable to facial injury when surgery is performed in the prone position. The nose, certain nerves, and especially the eyes are all at risk of compression injury any time an anesthetized patient is resting on his or her face during surgery. It is thus critically important that some means be provided for supporting the patient's head in a manner that protects the sensitive areas from any pressure during the surgical procedure.

2. Description of the Prior Art

Existing techniques for supporting the patient's head and protecting the face during prone-position procedures are generally unreliable and potentially ineffective. Commonly, anesthesiologists will use foam rubber donuts and stacks of small towels to support the head. However, the doctor frequently is operating in the blind, not knowing for certain the eyes and nose are not being subjected to pressure, since the position of the nose, mouth, or eyes can not be verified visually by the physician once the donut and towels have been installed.

Another prior art technique is to use a pair of pads connected by plastic arms with the forehead and chin resting on the pads. A major problem with this technique is that the total weight of the head is distributed on only these two points. This may cause skin sloughing at these two points.

An additional problem with prior art devices is their inability to provide for adjustment of the patient's head relative to the torso and support surface. Generally, these prior art devices limit the patient's head position to the "neutral" or centerline position. It is generally desirable however that a patient's head be adjustable relative to the torso and support surface to accommodate different surgical techniques and procedures.

A further limitation of prior art devices are their lack of any provision for the collection and draining away of any patient secretions during the surgical procedure. All patients to varying degrees "drool" during surgical procedures. Additionally, and of more concern, patients will often drain mucus or blood during the procedure. This is potentially hazardous to operating room personnel as it may expose them to infectious agents.

An illustration of these prior art devices and the problems associated therewith, is Voss, U.S. Pat. No. 4,752,064. Voss provides a means for supporting a patient's head over a large area by using a foam donut, thereby eliminating the problem of pressure points. However, there is no provision for drainage of any secretions. Neither is there any means for adjusting the position of the patient's head in either a rolling side to side direction or a pivot forward or backward. Additionally, due to the foam nature of the headrest, the physician is not able to visually verify the position of the patient's eyes and nose once the patient's head has contacted the headrest. Also, due to the fixed structure of the foam, points of relatively high pressure on the patient's face are still likely and somewhat unpredictable due to variations in facial structures.

Therefore, it is a prime objective of the present invention to provide an apparatus which is capable of supporting and protecting a patient's face during prone-position surgical procedures.

Another object of the present invention is to provide an apparatus which is capable of supporting a patient's face during prone-position procedures in a variety of selectively fixed angles relative to the patient's torso and the support surface.

Still another object of the present invention is to provide an apparatus which provides support for the patient's face over an extended region permitting the weight of the head to be distributed over a larger surface area.

Yet another object of the present invention is to provide an apparatus which permits the doctor to visually verify that the patient's nose, eyes, and other facial structures are not being exposed to any pressure during the surgery.

Another object of the present invention is to provide a facial support apparatus which is at least partially reusable.

Still another object of the invention is to provide an apparatus where the inflation of the mask may be varied to allow for maximum surface area contact with the skin, thereby minimizing the amount of pressure applied at any given point on the skin.

Finally, an object of the present invention is to provide an apparatus which permits the collection and drainage of any secretions by the patient during the surgical procedure.

SUMMARY OF THE INVENTION

The present invention is directed to a facial support mask apparatus for supporting the face of a patient in the prone position during surgical procedures in spaced relation above a support surface and in a variety of selectively fixed positions relative to the torso and the support surface.

The apparatus of the present invention comprises a plurality of transversely spaced longitudinal crescent arms; at least one cross-strut interconnected with the longitudinal crescent arms; an inflatable chamber adapted to contact the patient's forehead and sides of his face; attachment means for attaching the inflatable chamber to the crescent arms; and securement means for securing the mask to the patient's face. The apparatus provides a means whereby any adjacent pair of crescent arms are selectively engagable with the support surface to maintain the patient's head in spaced relation from the support surface, and to selectively fix the angle of the patient's head relative to the support surface. The apparatus may also include a secretion collection dish for draining away secretions during the surgical procedure. The crescent arms, cross-strut and dish may be all be formed from a single integral piece of material. Alternatively, the dish may be a separate unit placed adjacent the arms and struts. Alternatively, the dish may be integral with the surfaces which contact the patient's face, yet separable from the remainder of the apparatus. In this embodiment the dish/contact surface would potentially be single-use-disposable (or sterilizable) while the remainder would be reusable.

Additionally, the invention includes a novel method of supporting a patient's face during a surgical procedure in the prone position. The method's steps include providing a facial support mask for supporting a patient's face during surgical procedures in the prone position having a securement means for securing the mask to patient's face, a plurality of longitudinal crescent arms, at least one cross-strut interconnected to the longitudinal crescent arms, and a secretion collection dish, the crescent arms, cross-strut and dish, all being an integral part of a single piece of material, and an inflatable chamber secured to the crescent arms and adapted to contact the patient's forehead and sides of his face; anesthetizing the patient; placing the mask on patient's face such that no part of the mask contacts patient's eyes, nose, or lips; securing the mask to patient's face; securing the tracheal (breathing) tube to the mask if desired; rolling the patient into the prone position; adjusting the inflation of the chamber to obtain correct inflation pressure; adjusting the patient's head orientation; and draining of any patient secretions.

The invention thus provides great advantages over the prior art principally by allowing the doctor to visually verify that the patient's nose, eyes and other facial structures are not being subjected to any pressure. Another advantage lies in allowing the physician to adjust the position of the patient's head to selectively fixed angles to accommodate different surgical requirements and patient support surface configurations. Additionally, the present apparatus allows any secretions from the patient occurring during the surgical procedure to be collected and drained away without exposing the operating room personnel to any infectious agents. Further the inflation of the mask may be adjusted to maximize the surface area contacted thereby minimizing the pressure exerted on any given area of skin.

DESCRIPTION OF THE PREFERRED EMBODIMENT

Figure 1:
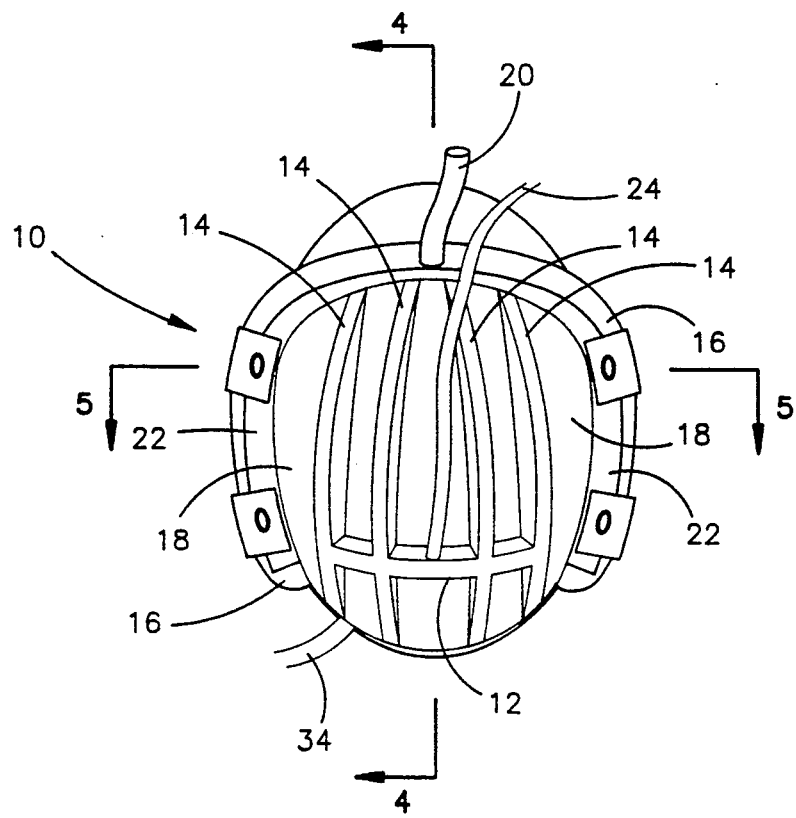
FIG. 1 is a frontal view of the apparatus showing major components of the invention.
Figure 3:
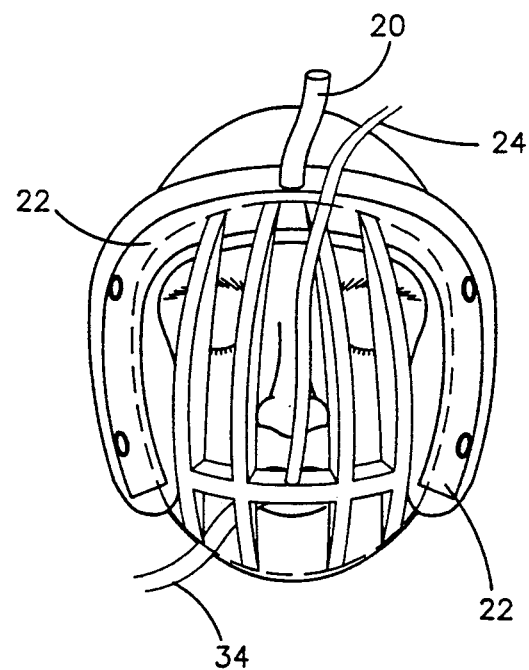
FIG. 3 is another front view of the apparatus showing its attachment to the patient's head.

The facial support mask 10 of the present invention is shown in FIGS. 1 and 3 as including a plurality of transversely spaced longitudinal crescent arms 14, interconnected with a cross-strut 12. Masks may be constructed in a variety of sizes, it being expected that three sizes will accommodate the vast majority of patients. In the preferred embodiment, the crescent arms 14 and cross-strut 12 are an integral part of the dish 18 which is connected to the inflatable chamber 16 by the attachment plate 22. In alternative embodiments, the dish 18 may be a separate piece which may be inserted into the mask 10 settling adjacent the crescent arms 14 and cross-strut 12. Alternatively, the cross-strut 12 and crescent arms 14 may be separate pieces which are connected to dish 18. Still further, the mask 10 may be constructed without longitudinal crescent arms 14 or cross-struts 12, and dish 18 would engage the support surface. In that embodiment, dish 18 could be integrally formed with inflatable chamber 16 or they may be formed of two separate pieces. In these latter embodiments, drainage would still be accomplished by collection of secretions at the drainage port 32 due to the generally curved lenticular shape of the dish 18. In the preferred embodiment, dish 18 and inflatable chamber 16 are constructed of disposable materials, thereby increasing the cost utility of the apparatus.

In the preferred embodiment, the dish 18 is constructed of clear material allowing the doctor to visually inspect the positioning of the mask relative to the patient's nose mouth and eyes to ensure no pressure is being placed on these facial structures. The dish 18 may be constructed of plastic or other similar material and may be disposable. The dish 18 not only serves to collect patient secretions but also to protect the face from any object which might be capable of poking through the spaces between struts 12 and crescent arms 14. When the crescent arms 14, cross-strut 12 and dish 18 are one integral piece, the crescent arms 14 and cross-strut 12 will have channels therein (FIG. 5) to facilitate the drainage of patient secretions. The cross-strut 12 and the longitudinal crescent arms 14 are bowed to facilitate this drainage and to allow for free movement of the patient's head into the desired position.

Inflatable chamber 16 is inflated/deflated by means of the fill valve 20. Once the mask has been placed on the patient's face and the patient placed in the prone position, the air in the inflatable chamber 16 may be adjusted to proper inflation to provide for sufficient clearance of the facial structures. The fill valve 20 is located atop the mask to provide the anesthetist with continuous access to the valve 20 throughout the operation. Ideally, the air pressure in the chamber 16 will be maintained at the minimum necessary to achieve facial structure clearance as this will maximize the amount of surface area contacted, minimizing the facial pressure at any given point.

Secretions by the patient during the surgical procedure are collected by the dish 18 and channeled by the crescent arms 14 and cross-strut 12 to the drainage tube 24. This allows any secretions to be drained away during the surgical procedure, thereby preventing exposure of the operating room personnel to infectious agents.

Since dish 18 and chamber 16 are disposable, the mask may be reused merely by replacing these components, thereby increasing the economic efficiency of the apparatus.

A notch or velcro strip (not shown) may be added to the lower portion of the mask to accommodate the tracheal tube 34.

Figure 2:
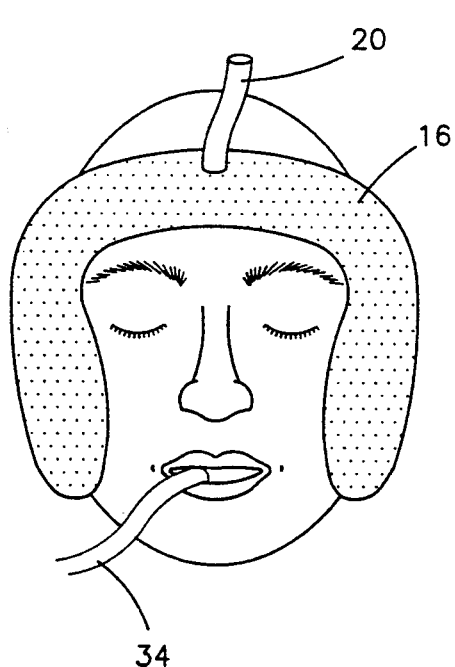
FIG. 2 is a front view of the inflatable chamber of the apparatus and its contact with the patient's face.
Figure 4:
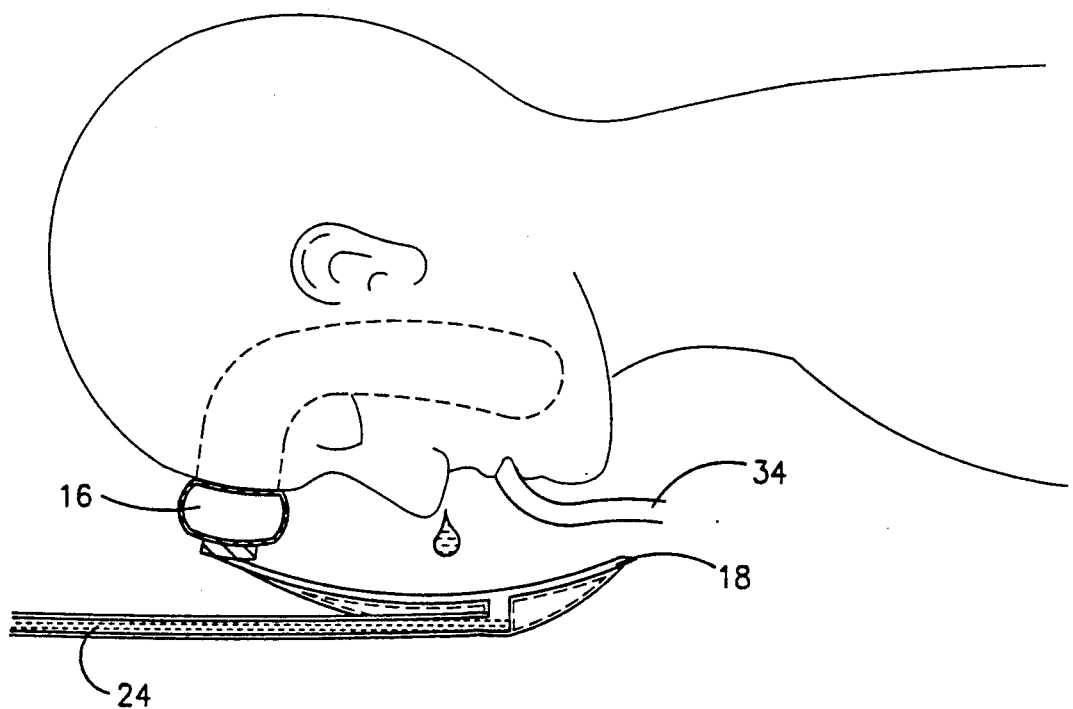
FIG. 4 is a side view of the apparatus showing its use in collecting any secretions from the patient during surgery and showing also the spaced relation at which the patient's face is maintained from the mask front and support surface.

FIGS. 2 and 4 demonstrate one of the principle advantages of the invention over the prior art. As can be seen in the two figures, the inflatable chamber 16 contacts the patient's face over a wide area. This allows the weight of the patient's head to be evenly distributed over this area preventing the placement of too much weight on any one spot and thereby preventing damage to the patient's skin in that area. Additionally, as can be seen in FIG. 4, the patient's eyes and nose are kept a safe distance from any contact with the mask 10 itself or the support surface. The inflation of chamber 16 can be adjusted to maximize the surface area contacting the face thereby minimizing the pressure exerted on the skin while still maintaining sufficient clearance of facial structures.

Figure 5:
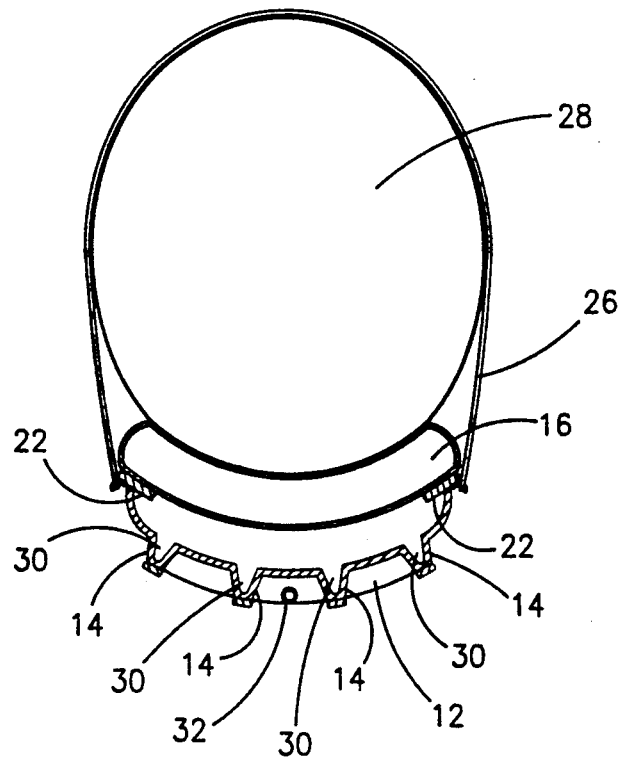
FIG. 5 is a top view showing the orientation of the mask to the head when it is secured thereto. Also shown is the channeling nature of the longitudinal crescent arms allowing the patient's secretions to be drained away.

FIG. 5 demonstrates the securement of the mask 10 to the patients head. FIG. 5 also illustrates the preferred embodiment where the crescent arms 14, cross-strut 12, and dish 18 are integrally formed from a single piece of material. In this embodiment, the crescent arms 14 and cross-strut 12 contain channels 30 which allow any secretions by the patient during surgery to be collected and drained away through the drainage port 32. FIG. 5 also demonstrates the large area over which the patient's head is supported by the inflatable chamber 16, thus eliminating any pressure points. Securement means 26 may be an elastic strap or the like and is used to secure the mask 10 to the patient's head. Numerous alternative types of securement devices may obviously be used.

It is also clear from FIG. 5 the patient's head may be rested in a "neutral" position relative to the patient's torso or rotated left or right. The mask allows the patient's head to rest in a rotated position since any adjacent crescent pair of arms 14 are engagable with the support surface and provide a stable contact therewith. Thus, depending on the nature of the surgical procedure or the support surface, the physician has the ability to adjust the orientation of the patient's head relative to the torso and support surface.

It is obvious that numerous other modifications and variations of the present invention are possible in view of the above teachings. For example, the size and shape of the inflatable chamber may be adjusted. Additionally, the protection dish and crescent arms/cross-struts may be made from a single piece of material as in the preferred embodiment or the dish may be inserted into the mask, resting adjacent the cross-strut and crescent arms. Of course the dish itself may be constructed of numerous types of materials, the preferred material being plastic. Still further, the mask may be constructed without crescent arms or cross-struts. Additionally, a notch or velcro strip may be added in the lower part of the mask to accommodate a tracheal tube.

Therefore it is to be understood that the above description is in no way intended to limit the scope of protection of the claims and is representative only of one of the several possible embodiments of the present invention.

There has thus been shown and described an invention which accomplishes at least all of the stated objects.

I claim:

1. A facial support mask for supporting the face of a patient in the prone position during surgical procedures, in a spaced relation above a support surface comprising:
   an inflatable chamber adapted to contact the patient's forehead and sides of his face;
   a solid dish having a drainage hole wherein said solid dish is curved in order to generally conform to a user's face such that it may roll on a supporting surface;
   attachment means for attaching said dish directly to said inflatable chamber at a position for collection of fluid from said patient's face while said patient is supported in said prone position; and
   securement means for securing said mask and dish to the patient's face wherein the patient's face is maintained in a spaced relation from the support surface.

2. The invention of claim 1 wherein said inflatable chamber is generally "C" shaped.

3. The invention of claim 2 wherein said dish is constructed of a generally clear material.

4. A facial support mask for supporting the face of a patient in the prone position during surgical procedures in a spaced relation above a support surface comprising:
   a plurality of transversely spaced longitudinal crescent arms;
   at least one cross-strut interconnected with said longitudinal crescent arms;
   a generally lenticular shaped dish integrally formed with said longitudinal crescent arms and cross-strut and having interior and exterior surfaces, said crescent arms and cross-strut forming troughs in the interior surface of said dish and ridges on the exterior surface thereof;
   an inflatable chamber adapted to contact the patient's forehead and sides of his face;
   attachment means for attaching said inflatable chamber to said crescent arms; and
   securement means for securing said mask to the patient's face;
   any adjacent pair of crescent arms being selectively engagable with the support surface to maintain the patient's head in spaced relation from the support surface, and to selectively fix the angle of the patient's head relative to the support surface.

5. The invention of claim 4 wherein said dish is constructed of clear plastic material.

6. The invention of claim 5 wherein the attachment means is an attachment plate attached to said dish and operative to secure said inflatable chamber to said lenticular shaped dish.

7. A facial support mask for supporting the face of a patient in the prone position during surgical procedures, in a spaced relation above a support surface comprising:
   a plurality of transversely spaced longitudinal crescent arms;
   at least one cross-strut interconnected with said longitudinal crescent arms;
   a solid dish having a drainage hole therein and adapted to be placed adjacent said longitudinal crescent arms and cross-struts and operative to collect and drain any accumulated patient secretions;
   an inflatable chamber adapted to contact the patient's forehead and sides of his face;
   attachment means for attaching said inflatable chamber to said crescent arms; and
   securement means for securing said mask to the patient's face;
   any adjacent pair of crescent arms being selectively engagable with the support surface to maintain the patient's head in spaced relation from the support surface, and to selectively fix the angle of the patient's head relative to the support surface.

8. The invention of claim 7 wherein said cross strut is generally perpendicular to said crescent arms.

9. The invention of claim 8 wherein said inflatable chamber is generally "C" shaped.

10. The invention of claim 9 wherein said dish is constructed of a clear material.

* * * * *